US009410543B2

(12) United States Patent
Tokuo et al.

(10) Patent No.: US 9,410,543 B2
(45) Date of Patent: Aug. 9, 2016

(54) PUMP FOR LIQUID CHROMATOGRAPH, AND LIQUID CHROMATOGRAPH

(75) Inventors: Kenichiro Tokuo, Hitachinaka (JP); Kenji Hiraku, Kasumigaura (JP); Hironori Kaji, Hitachinaka (JP); Daisuke Akieda, Hitachinaka (JP); Kimihiko Ishii, Hitachinaka (JP); Naoya Yasuhara, Hitachinaka (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 605 days.

(21) Appl. No.: 13/808,660

(22) PCT Filed: Jul. 20, 2011

(86) PCT No.: PCT/JP2011/066421
§ 371 (c)(1),
(2), (4) Date: Jan. 7, 2013

(87) PCT Pub. No.: WO2012/014741
PCT Pub. Date: Feb. 2, 2012

(65) Prior Publication Data
US 2013/0104631 A1 May 2, 2013

(30) Foreign Application Priority Data

Jul. 29, 2010 (JP) .................................. 2010-169962

(51) Int. Cl.
*F04B 17/03* (2006.01)
*F04B 13/00* (2006.01)
(Continued)

(52) U.S. Cl.
CPC ................. *F04B 17/03* (2013.01); *F04B 13/00* (2013.01); *F04B 23/06* (2013.01); *F04B 49/06* (2013.01);
(Continued)

(58) Field of Classification Search
CPC ........ F04B 13/00; F04B 23/06; F04B 49/065; F04B 17/03; F04B 49/06; F04B 49/08; F04B 2203/0202; F04B 2205/03; F04B 2205/05; G01N 30/02; G01N 30/34; G01N 2030/326
USPC ............... 73/61.56; 417/245, 410.1, 254, 265
See application file for complete search history.

(56) References Cited

U.S. PATENT DOCUMENTS 4,352,636 A * 10/1982 Patterson et al. ............... 417/22
4,883,409 A 11/1989 Strohmeier et al.
(Continued)

FOREIGN PATENT DOCUMENTS

DE 103 29 314 A1 5/2004
JP 1-104989 4/1989
(Continued)

OTHER PUBLICATIONS

JP Office Action of Appln. No. 2010-169962 dated Mar. 11, 2014 with English translation.
(Continued)

*Primary Examiner* — Hezron E Williams
*Assistant Examiner* — Marrit Eyassu
(74) *Attorney, Agent, or Firm* — Baker Botts L.L.P.

(57) ABSTRACT

A pump controller causes a first plunger pump and a second plunger pump connected in series or in parallel to perform intake and compression actions alternately at substantially constant cycles, sets a pressurizing chamber of one of the plunger pumps to a state of a higher pressure than the pressurizing chamber of the other plunger pump, and performs flow rate control by adjusting lift amounts of the first plunger and the second plunger. Thus, it is possible to provide a pump for liquid chromatograph, and a liquid chromatograph, which are capable of reducing pulsations even when an ejection flow rate is changed.

17 Claims, 12 Drawing Sheets

(51) Int. Cl.
*F04B 23/06* (2006.01)
*F04B 49/06* (2006.01)
*G01N 30/32* (2006.01)
*G01N 30/02* (2006.01)
*F04B 49/08* (2006.01)
*G01N 30/34* (2006.01)

(52) U.S. Cl.
CPC .............. *F04B 49/065* (2013.01); *F04B 49/08* (2013.01); *G01N 30/02* (2013.01); *G01N 30/32* (2013.01); *G01N 30/34* (2013.01); *F04B 2203/0202* (2013.01); *F04B 2205/03* (2013.01); *F04B 2205/05* (2013.01); *G01N 2030/326* (2013.01)

(56) References Cited

U.S. PATENT DOCUMENTS

| | | | | |
|---|---|---|---|---|
| 5,823,747 | A * | 10/1998 | Ciavarini | F04B 49/06 210/101 |
| 6,923,916 | B1 * | 8/2005 | Hiraku et al. | 210/656 |
| 7,631,542 | B2 * | 12/2009 | Weissgerber | 73/61.56 |
| 2001/0027659 | A1 * | 10/2001 | Ota | F04B 27/1804 62/228.3 |
| 2004/0146417 | A1 * | 7/2004 | Dunn | F04B 17/046 417/417 |
| 2004/0164013 | A1 | 8/2004 | Takao et al. | |
| 2005/0023205 | A1 * | 2/2005 | Hiraku et al. | 210/198.2 |
| 2005/0213091 | A1 * | 9/2005 | Fujita | 356/326 |
| 2006/0000759 | A1 | 1/2006 | Takao et al. | |
| 2007/0084766 | A1 | 4/2007 | Ishii et al. | |
| 2008/0101970 | A1 * | 5/2008 | Witt et al. | 417/521 |
| 2008/0296209 | A1 | 12/2008 | Takao et al. | |
| 2009/0047137 | A1 * | 2/2009 | Stenberg | F04B 43/0081 417/44.1 |
| 2009/0193879 | A1 * | 8/2009 | Yasuhara et al. | 73/61.56 |
| 2010/0288027 | A1 | 11/2010 | Ishii et al. | |

FOREIGN PATENT DOCUMENTS

| | | |
|---|---|---|
| JP | 2005-55179 | 3/2005 |
| JP | 2007-057539 | 3/2007 |
| JP | 2007-113439 | 5/2007 |
| JP | 2008-264640 | 11/2008 |
| JP | 2009-180617 | 8/2009 |

OTHER PUBLICATIONS

Office Action, mailed Jul. 14, 2015, which issued during the prosecution of German Patent Application No. 11 2011 102 529.7, which corresponds to the present application (with English translation attached).

* cited by examiner

Fig. 4
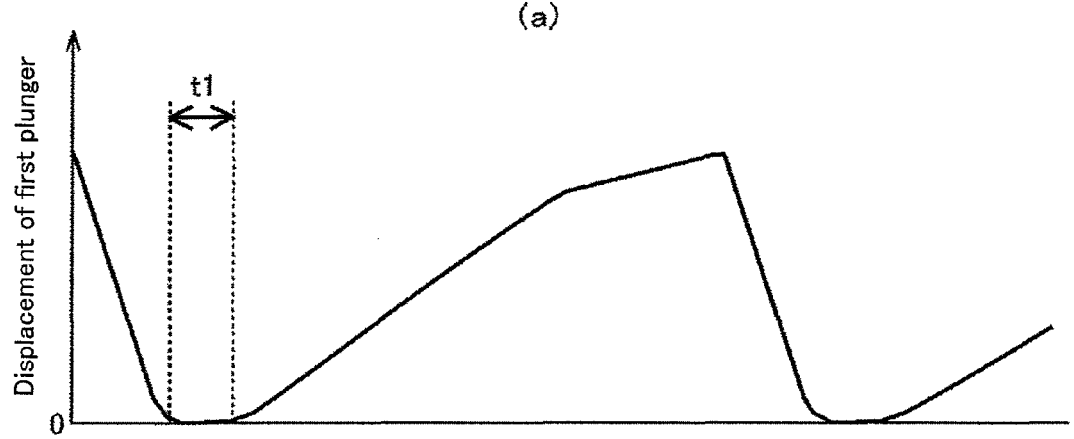
(a)
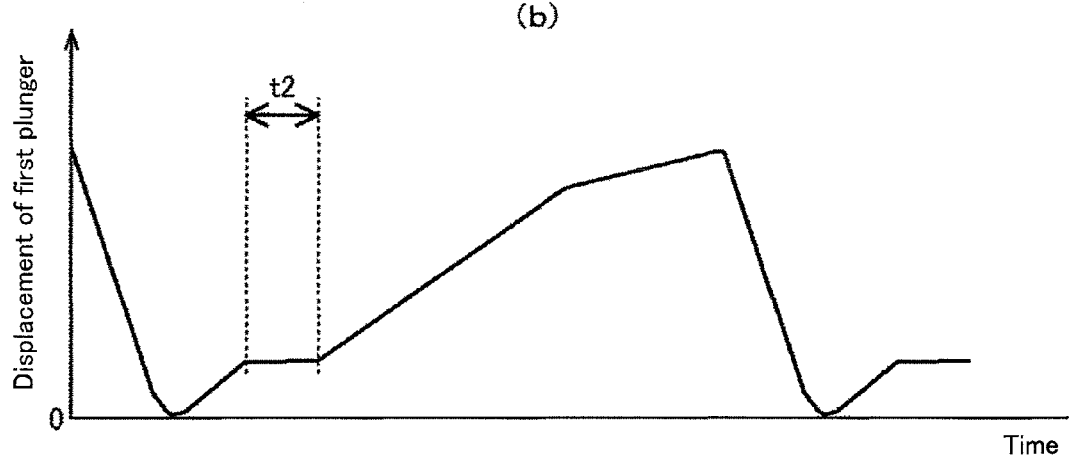
(b)

PUMP FOR LIQUID CHROMATOGRAPH, AND LIQUID CHROMATOGRAPH

TECHNICAL FIELD

The present invention relates to a pump for liquid chromatograph, and a liquid chromatograph.

BACKGROUND ART

A conventionally known pump structure used in a liquid chromatograph includes two plunger pumps which are connected in series or in parallel in such a manner that a first plunger pump and a second plunger pump perform coordinated operations to reduce pulsations (see Patent Document 1, for example). The configuration disclosed in Patent Document 1, for instance, is the configuration in which the first plunger pump and the second plunger pump are connected in series and reciprocating motions of the plungers are driven by use of cams. In phase 1 of a pumping operation, a downstream pump 1a performs an intake action (at an ejection flow rate of 0) while an upstream pump 1b performs ejection at a flow rate of Q, and a total ejection amount is therefore equal to Q. In phase 2, both of the pumps perform ejection at a flow rate of Q/2, and the total ejection amount is therefore equal to Q. In phase 3, the upstream pump 1b performs an intake action at a flow rate of 3Q/2 while the downstream pump 1a performs an ejection action at a flow rate of 3Q/2+Q, and the total ejection amount is therefore equal to Q. In this way, the pulsations are reduced by stably feeding a liquid while maintaining the total flow rate of Q at any time regardless of the intake actions of the pumps.

Meanwhile, there is also proposed a technique for suppressing occurrence of pulsations by controlling the number of revolutions of a motor for driving a plunger by use of values detected by a plunger-position detection sensor and a flow rate sensor (see Patent Document 2, for example).

However, the inventions described in Patent Document 1 and Patent Document 2 do not take into consideration the processing accuracy, assembly accuracy, and control accuracy of the pumps. For example, a cyclic pulsation occasionally occurs due to a backlash or a dimensional looseness in a cam mechanism for driving a plunger pump, manufacturing accuracy, vibration at the time of a change in speed, or other factors. A pulsation thus caused leads to a fluctuation in a flow rate of a solvent that passes through a separation column in a liquid chromatograph or a mixing ratio of a solvent, and to deterioration in accuracy of a detection result shown on a chromatogram. In this regard, there has been a demand for a technique for suppressing a pressure pulsation of a pump for liquid chromatograph while taking into consideration an actual device configuration.

Another technique is known in which a mixer or a pulsation absorbing damper is provided to piping, so that a pulsation caused by a pump in a liquid chromatograph is not transmitted to a separation column (see Patent Document 3, for example). Although such devices are effective in attenuating a pulsation at a specific cycle, the devices can hardly reduce pulsations of all cycles because a pump for liquid chromatograph, which is a subject of the present invention, is configured to control an ejection flow rate by changing a drive cycle.

PRIOR ART DOCUMENTS

Patent Documents

Patent Document 1: Japanese Patent Application Publication No. 2009-180617
Patent Document 2: Japanese Patent Application Publication No. 2007-113439
Patent Document 3: Japanese Patent Application Publication No. 2008-264640

SUMMARY OF THE INVENTION

Problem To Be Solved by the Invention

An object of the present invention is to provide a pump for liquid chromatograph, and a liquid chromatograph, which are capable of reducing pulsations even when an ejection flow rate is changed.

Means for Solving the Problem

To solve the problem, an embodiment of the present invention includes a first plunger pump and a second plunger pump connected in series or in parallel, and a pump controller. The embodiment is characterized in that the pump controller: causes the first plunger pump and the second plunger pump, which are connected in series or in parallel, to perform intake and compression actions alternately at substantially constant cycles; at least sets a pressurizing chamber of one of the plunger pumps to a state of a higher pressure than a pressurizing chamber of the other plunger pump; and performs flow rate control by adjusting lift amounts of the first plunger and the second plunger.

This description incorporates the contents of the specification and/or the drawings disclosed in Japanese Patent Application No. 2010-169962 which forms the basis of the priority claim of the present application.

Effects of the Invention

The present invention can provide a pump for liquid chromatograph, and a liquid chromatograph, which are capable of reducing pulsations even when an ejection flow rate is changed.

BRIEF DESCRIPTION OF THE DRAWINGS

FIG. 4 shows graphs of temporal variations of displacements of a first plunger.

MODES FOR CARRYING OUT THE INVENTION

Figure 1:
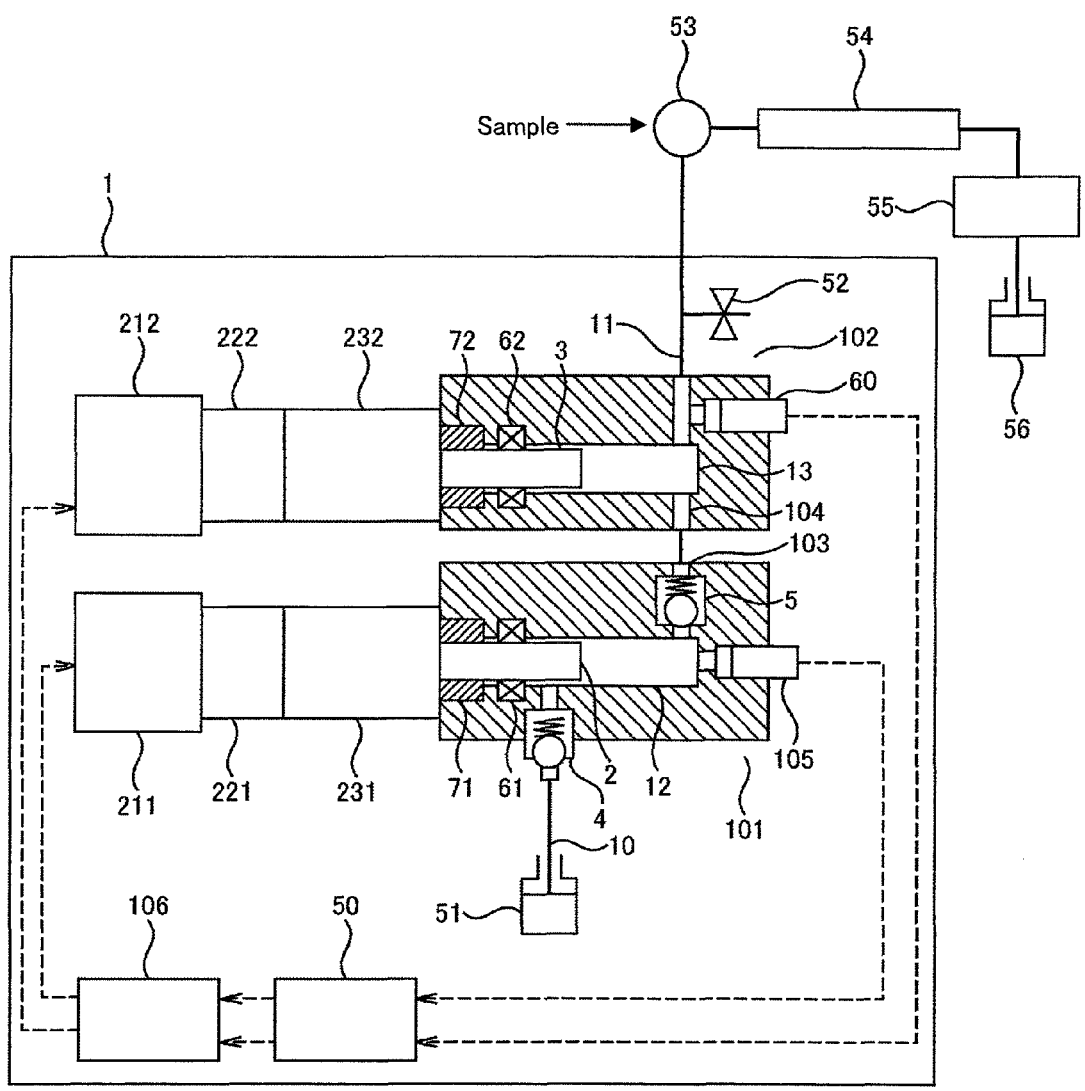
FIG. 1 is a configuration diagram showing a configuration of a liquid chromatograph.

An embodiment of the present invention will be described below with reference to the drawings.

Embodiment

First of all, a configuration of the present invention is summarized as follows.

A pump for liquid chromatograph according to the present invention includes a first plunger pump and a second plunger pump connected in series or in parallel, a first plunger configured to reciprocate inside a pressurizing chamber of the first plunger pump, a second plunger configured to reciprocate inside a pressurizing chamber of the second plunger pump, at least one electric motor configured to generate rotative power, a power transmission mechanism configured to convert the rotative power of the electric motor into linear reciprocating power and to provide the first plunger and the second plunger with drive power, a motor driver configured to control the electric motor, a first pressure sensor provided in the pressurizing chamber of the first plunger pump, a second pressure sensor provided in a channel on a downstream side of the second plunger, and a pump controller configured to read measurement values of the pressure sensors and to provide the motor driver with an instruction. Here, the pump controller is characterized in that the pump controller causes the first plunger pump and the second plunger pump to perform intake and compression actions alternately at substantially constant cycles; sets the pressurizing chamber of one of the plunger pumps to have a higher pressure than the pressurizing chamber of the other plunger pump; and performs flow rate control by adjusting lift amounts of the first plunger and the second plunger. In this way, the pump for liquid chromatograph can generate pulsations at a constant cycle synchronously with the action cycles of the plunger pumps regardless of ejection flow rates of the plunger pumps.

The pump for liquid chromatograph is preferably configured to define a resting period to set an action speed of the second plunger to zero, and to perform high-pressure liquid feeding only with the first plunger pump during the resting period. More preferably, the pump controller is configured to adjust a length of the above-mentioned resting period and the lift amount of the first plunger depending on an amount of liquid feeding. In this way, a total ejection amount is controlled by the lift amount of the first plunger pump and the flow rate control is simplified accordingly.

Preferably, the pump controller is configured to perform control in such a manner that the first plunger maintains a state where an action speed is set to zero for a predetermined period within a time between a timing when the first plunger pump terminates an intake action and a timing when the second plunger pump terminates a compression action. In this way, even when time required for compression varies due to a change in an ejection pressure of the plunger pump, a flow rate, or a solvent, a single cycle of a drive cycle of each plunger pump can be adjusted to have a substantially constant length by adjusting such a standby period.

A point of time to start the control for setting the speed of the first plunger to zero is preferably a point of time when a pressure in the first plunger pump is substantially equal to a pressure in the second plunger pump. Thus, a pre-compression operation can be carried out reliably.

Preferably, the pump controller is configured to change the period in which the action speed is set to zero depending on a detection value of a pressure detecting means, and to maintain the drive cycle of each of the first plunger pump and the second plunger pump substantially at a constant length. This configuration makes it easier to achieve a target value of the drive cycle of each pump by adjusting the period in which the action speed is set to zero, i.e., the standby period.

A specific upper limit value is preferably set to an absolute value of acceleration of each of the first plunger and the second plunger. In this way, a speed change is made smoother and an influence of a backlash, vibration or the like is reduced at the time of occurrence of the speed change. Hence, pulsations are reduced.

Preferably, the speeds of both of the plungers are once set to zero at a point of time when the pressure in the first plunger pump is substantially equal to the pressure in the second plunger pump. This configuration eliminates occurrence of intermittent speed changes at the time of switching the plunger pump that performs liquid feeding. Hence, pulsations are reduced.

A first ejection channel is preferably connected to a second intake channel, and each of a first intake channel and the first ejection channel is preferably provided with a check valve. In other words, the two plunger pumps are connected in series. Thus, the above-described driving method can be effectively realized.

Alternatively, the first ejection channel is connected to a second ejection channel and the first intake channel is connected to the second intake channel. Moreover, a check valve is provided in each of the first and second intake channels and ejection channels. In other words, the two plunger pumps are connected in parallel. This configuration can also realize the above-describe driving method effectively.

The pressure detecting means is preferably provided in each of a first pressurizing chamber and a second pressurizing chamber. This configuration enables a reliable judgment on whether the pressures of the first plunger pump and the second plunger pump are substantially equal.

Preferably, a pressure sensor is provided in each of the first pressurizing chamber and the second ejection channel. In this way, a pressure equivalent to that in the second pressurizing chamber can be detected in the second ejection channel. Thus, volume efficiency of the plunger pump can be improved while reducing a dead volume caused by providing a pressure sensor in the second pressurizing chamber.

When amounts of liquid feeding by the first plunger pump and the second plunger pump are changed during a gradient operation mode in which a liquid is fed while changing a concentration ratio of multiple types of solvents, the pump controller is preferably configured to perform flow rate control by adjusting the lift amounts of the first plunger and the second plunger so as to maintain the drive cycles of the plungers at substantially constant lengths. In this way, a generation cycle of pulsations can be kept constant while avoiding an influence of a mixing ratio of solvents which steadily changes in the gradient operation mode. In addition, a characteristic of the liquid chromatograph can be improved by setting the generation cycle of pulsations to such a cycle that a damper or a mixer operates efficiently.

Preferably, the power transmission mechanism includes a cam. In a cam phase where a differential value $dL/d\theta$ of a rotational angle $\theta$ relative to a lift amount L of the cam varies, a cam phase is preferably established by changing a rotational speed of the electric motor in such a manner that a product of the differential value dL/dθ and the rotational speed of the electric motor becomes substantially constant as compared to values preceding and subsequent thereto. Here, it is possible to provide a desired rate of change in the rotational speed of the electric motor by adjusting a profile of the differential value dL/dθ. For example, when the differential value dL/dθ is instantaneously doubled, the rotational speed of the motor can be instantaneously reduced to half while keeping the ejection flow rate constant.

Two electric motors are preferably provided so that the two plunger pumps can be driven independently of each other. This configuration makes it possible to provide various liquids having different physical properties with appropriate amounts of pre-compression and thereby to ensure the degree of freedom for reducing pulsations.

A liquid chromatograph preferably includes a first pump configured to feed a first eluent, a second pump configured to feed a second eluent, a mixer configured to mix the first eluent and the second eluent, an injector configured to inject a sample into the eluents mixed by the mixer, a separation column configured to separate the sample injected into the eluent into its components, and a detector configured to allow inflow of the eluents in which the sample is separated into the components and to detect the components by irradiating the eluent with light. The liquid chromatograph is characterized in that each of the first pump and the second pump includes a first plunger pump and a second plunger pump connected in series, and a pump controller. Here, the pump controller: causes the first plunger pump and the second plunger pump to perform intake and compression actions alternately at substantially constant cycles; at least sets a pressurizing chamber of one of the plunger pumps to a state of a higher pressure than a pressurizing chamber of the other plunger pump; and performs flow rate control by adjusting lift amounts of the plunger of the first plunger pump and the plunger of the second plunger pump. As described above, when two types of eluents are used, pulsations can be reduced by providing dedicated pumps for feeding each of the eluents, each pump being provided with the above-described characteristic features of the present invention.

Now, the embodiment of the present invention will be described with reference to the drawings.

FIG. 1 is a configuration diagram showing a configuration of a liquid chromatograph. In FIG. 1, a pump 1 for liquid chromatograph mainly includes a first plunger pump 101, a second plunger pump 102, a pump controller 50, and a motor driver 106. A first intake channel 10, a first ejection channel 103, and a first pressurizing chamber 12 are formed in the first plunger pump 101. A check valve 4 and a check valve 5 are respectively located on the first intake channel 10 and the first ejection channel 103. Each check valve is biased in one direction by a spring and serves as a check valve which restricts a direction of flow of a solvent. A second intake channel 104, a second ejection channel 11, and a second pressurizing chamber 13 are formed in the second plunger pump 102. The first ejection channel 103 is connected to the second intake channel 104. In other words, the first plunger pump 101 and the second plunger pump 102 are arranged in series and the first plunger pump 101 is located on an upstream side. A first plunger 2 as a pressurizing member is slidably held on the first plunger pump 101 by a bearing 71. A second plunger 3 as another pressurizing member is slidably held on the second plunger pump 102 by a bearing 72.

Rotation of an electric motor 211 is decelerated by a deceleration device 221 and is converted into a linear motion by a linear motion device 231 to cause the first plunger 2 to reciprocate. Similarly, rotation of an electric motor 212 is decelerated by a deceleration device 222 and is converted into a linear motion by a linear motion device 232 to cause the second plunger 3 to reciprocate.

Here, the deceleration device 221 and the linear motion device 231 can be collectively referred to as a power transmission mechanism device in a broader sense because the combination of these devices enables amplification of rotative power of the electric motor 211 and conversion of the power into linear motion power. A concrete example of the deceleration device 221 may include a spur gear, a pulley, a planetary gear, a worm gear, and the like. A reason for providing the deceleration device is to increase torque of the electric motor. In this context, it is not always necessary to provide the deceleration device if the electric motor is capable of generating sufficient torque. A concrete example of the linear motion device 231 may include a ball screw, a cam, a rack and pinion, and the like but is not particularly limited in implementing the present invention. A sealing 61 prevents a liquid leakage from the first pressuring chamber 12 while a sealing 62 prevents a liquid leakage from the second pressuring chamber 13. Based on signals from pressure sensors 60 and 105, the pump controller 50 provides the motor driver 106 with instruction values to provide the electric motors 211 and 212 with drive power.

A solvent in a solvent container 51 is taken into the first pressuring chamber 12 in the first plunger pump 101 through the first intake channel 10, pressurized and taken into the second pressurizing chamber 13 in the second plunger pump 102 through the first ejection channel 103 and the second intake channel 104, and then pressurized and ejected from the second ejection channel 11. Thereafter, a sample which is an analysis object is injected into the solvent using an injector 53. The solvent mixed with the sample enters a separation column 54 to be separated into components. Then, a detector 55 detects data for a component analysis. The separation column 54 is filled with minute silica gel particles and a load pressure in a range from several tens of megapascals to more than a hundred megapascals is generated in each plunger pump due to fluid resistance of the solvent flowing through gaps among the silica gel particles. The magnitude of the load pressure varies depending on the diameter of the separation column and a flow rate of the solvent flowing therethrough.

Figure 2:
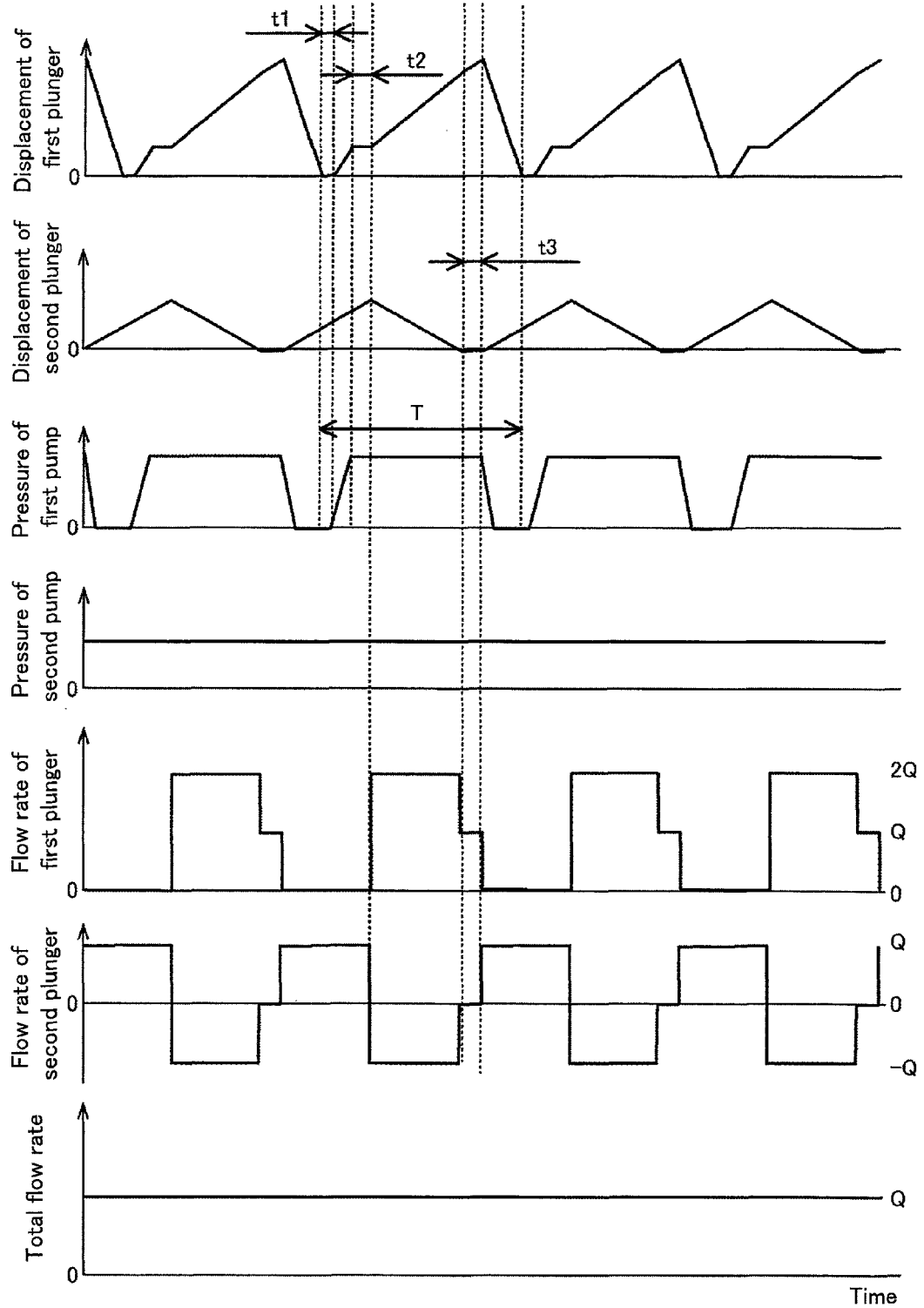
FIG. 2 shows graphs of temporal variations of displacements, pressures, and flow rates of plungers.

FIG. 2 shows graphs of temporal variations of displacements, pressures, and flow rates of the plungers. A method of operating the pump for liquid chromatograph will be described by using the graphs. In FIG. 2, the horizontal axis in each graph indicates time while vertical axes indicate, from top down, a displacement of the first plunger 2, a displacement of the second plunger 3, a pressure detected by the pressure sensor 105, a pressure detected by the pressure sensor 60, an extruded volume (corresponding to a flow rate) by the first plunger 2, an extruded volume (corresponding to a flow rate) by the second plunger 3, and a total flow rate passing through the second ejection channel 11.

As can be seen from the temporal variations of the displacement of the first plunger 2 and the displacement of the second plunger 3 in FIG. 2, during normal operation, the first plunger 2 and the second plunger 3 alternately perform intake actions and compression actions to continuously and stably feed a liquid at a constant flow rate as the pump for liquid chromatograph as a whole. The actions of the first plunger 2 and the second plunger 3 are controlled by causing the pump controller 50 to provide the motor driver 106 with instruction values and thereby driving the electric motors 211 and 212. A state of operation will be described below.

During the intake action of the first plunger 2, the second plunger 3 performs the compression action and feeds the solvent to the separation column 54. At this time, the extruded volume by the first plunger 2 is equal to zero and the solvent is solely fed by the second plunger 3. In this case, when the extruded volume by the second plunger 3 is defined as Q [mL/s (milliliters per second)], the flow rate passing through the second ejection channel 11 in the pump for liquid chromatograph as a whole is equal to Q [mL/s]. The extruded volume Q [mL/s] is calculated as a product of an action speed V [cm/s] and a cross-sectional area S [cm$^2$] of the second plunger 3.

Thereafter, the first plunger 2 terminates the intake action, pauses for a predetermined period t1, and then starts the compression action. From a point of time when the pressure in the first pressurizing chamber 12 becomes equal to the pressure in the second pressurizing chamber 13, the first plunger 2 pauses for a predetermined period t2. Here, a timing to pause for the period t2 is judged by the pump controller 50. For example, the pump controller 50 judges the timing to pause for the period t2 by referring to the pressures detected by the pressure sensor 105 and the pressure sensor 60 and judging that the pressure in the first pressurizing chamber 12 becomes equal to the pressure in the second pressurizing chamber 13. Alternatively, the timing to pause may be defined as a period which is predetermined on the basis of an operating condition, such as a time when the pressures are expected to become equal. During this period, the second plunger 3 continues the compression action at a constant speed whereby the flow rate passing through the second ejection channel 11 is kept at Q [mL/s] in the pump for liquid chromatograph as a whole.

Then, as the second plunger 3 terminates the compression action and starts the intake action, the first plunger 2 starts the compression action. The flow rate of the extruded volume by the first plunger 2 is regulated to be greater by Q [mL/s] than the flow rate of the volume taken in by the second plunger 3. Thus, the solvent constantly passes through the second ejection channel 11 at the net flow rate Q [mL/s] in the pump 1 for liquid chromatograph as a whole. Here, a timing for the second plunger 3 to terminate the compression action is determined and judged by the pump controller 50.

Then, after terminating the intake action, the second plunger 3 pauses for a predetermined period t3. During this period, the first plunger 2 reduces its speed and continues the compression action. The flow rate of the extruded volume by the first plunger 2 at this time is set to Q [mL/s]. Thus, the solvent constantly passes through the second ejection channel 11 at the net flow rate Q [mL/s] in the pump 1 for liquid chromatograph as a whole. Here, a timing for the second plunger 3 to terminate the intake action is determined and judged by the pump controller 50. Then, as the first plunger 2 terminates the compression action and starts the intake action, the second plunger 3 starts the compression action. Hence, the same actions are repeated.

Figure 3:
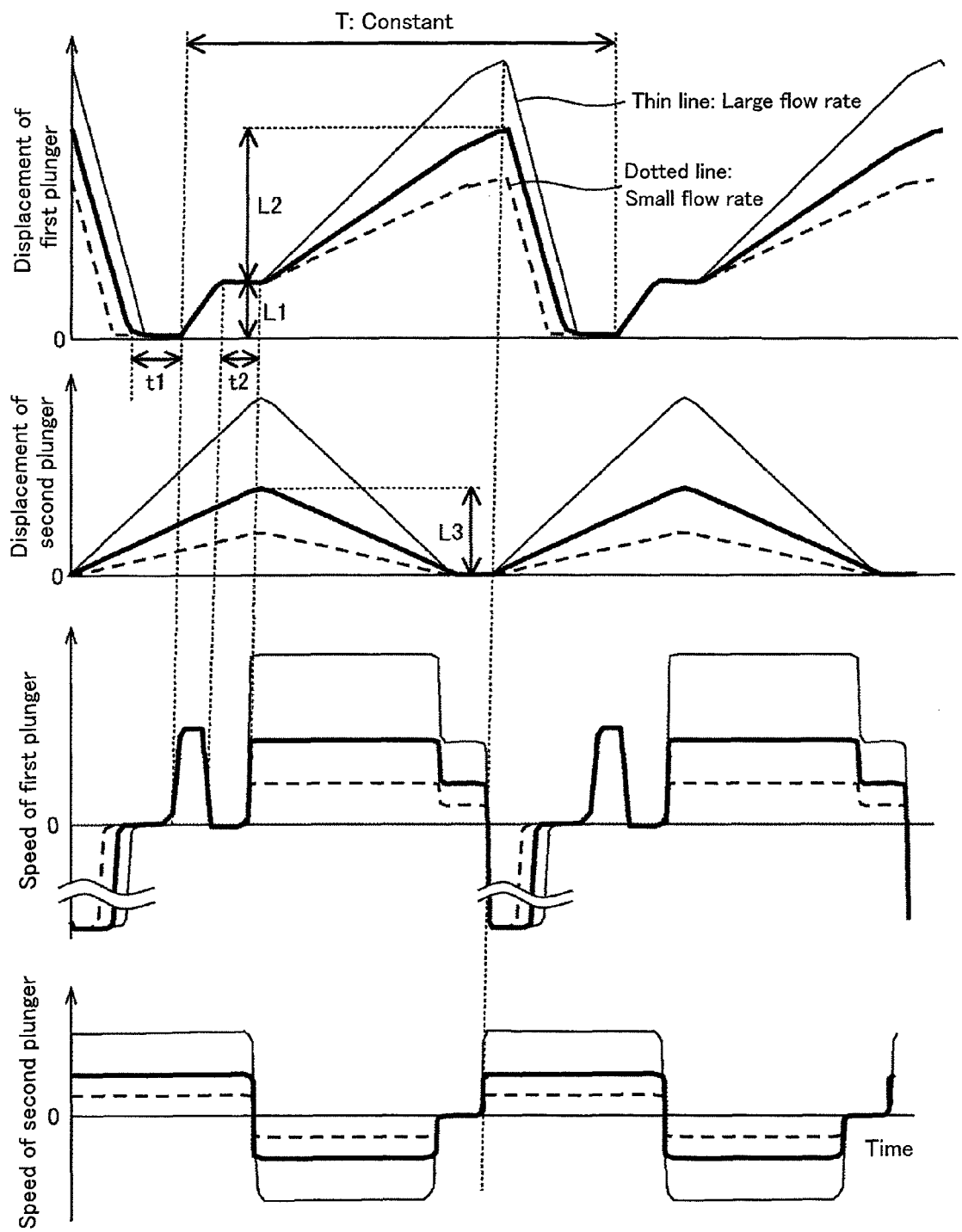
FIG. 3 shows graphs of temporal variations of displacements and speeds of the plungers.

FIG. 3 shows graphs of temporal variations of displacements and speeds of the plungers. Now, a method of controlling a flow rate by the pump controller 50 will be described below. In this embodiment, the flow rate control is achieved by adjusting lift amounts of the first plunger 2 and the second plunger 3. The lift amount of the first plunger 2 is mainly a sum of a lift amount L1 necessary for raising the pressure of the liquid up to an ejection pressure (which is called pre-compression) and a lift amount L2 for pressure feeding the pre-compressed liquid. The lift amount L2 is increased as indicated with a thin line when the pump 1 for liquid chromatograph has a large flow rate as a whole. At this time, a lift amount L3 of the second plunger 3 is also increased along with the lift amount L2. In the meantime, an overall drive cycle T is adjusted to be constant by using the period t1 and the period t2 as buffers. This makes it possible to control the flow rate without changing the drive cycle T of the plunger pumps. Meanwhile, drive profiles in the case of a small flow rate are indicated with dotted lines. In this case, the lift amount L2 and the lift amount L3 are reduced. As shown in the graphs, the drive cycle T of the plunger pumps is kept constant in this case as well. By maintaining the constant drive cycle T of the plunger pumps irrespective of the controlled flow rate, it is possible to set the drive cycle of the plunger pumps to a frequency range that can achieve a fine pulsation absorbing performance of a damper, for example, and thereby to reduce pulsations.

FIG. 4 shows graphs of temporal variations of displacements of the first plunger. FIG. 4(a) shows a case of depicting the period t1 in which the action speed of the first plunger 2 becomes zero while setting the period t2 substantially equal to zero. FIG. 4(b) shows a case of depicting the period t2 in which the action speed of the first plunger 2 becomes zero while setting the period t1 substantially equal to zero. Since the lengths of the period t1 and the period t2 can be freely set, it is possible to perform control setting by the pump controller 50 as shown in FIG. 4 when needed.

Figure 5:
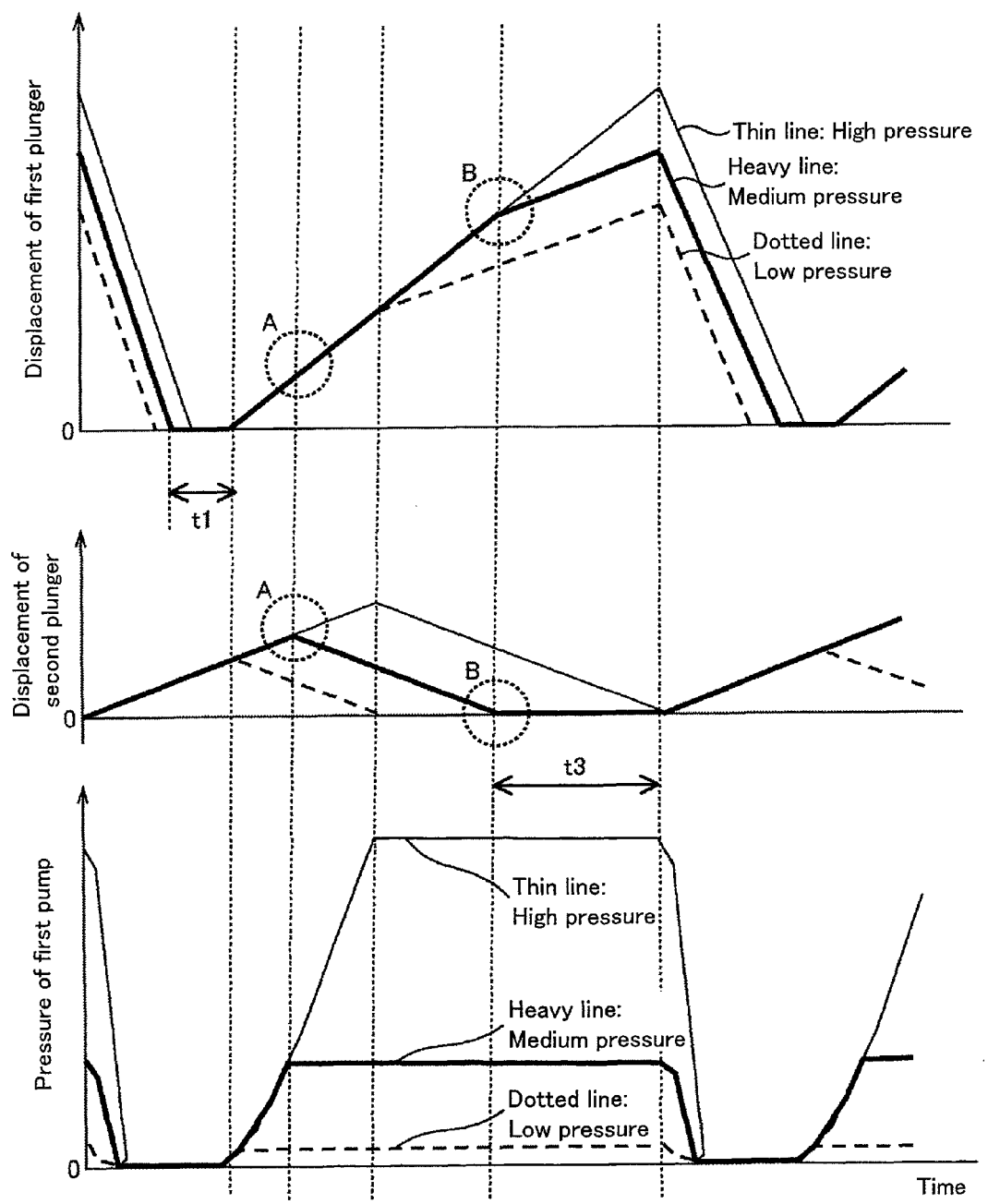
FIG. 5 shows graphs of temporal variations of displacements of the plungers and pressures of a first pump.

FIG. 5 shows graphs of temporal variations of displacements of the plungers and pressure of the first pump 101. The graphs show examples of drive profiles created by the pump controller 50 when ejection pressures are different. The graphs show, from top down, displacements of the first plunger 2, displacements of the second plunger 3, and pressure of the first plunger pump 101. The pressure of the first plunger pump 101 is pressure detected by the pressure sensor 60. After the lapse of the period t1, as the first plunger 2 pressurizes the solvent and starts ejection, the second plunger 3 starts the intake action at a point A and continues the intake action until a point B. The drive profiles indicated with thin lines show the case of high-pressure ejection. Since a relatively long stroke is required for achieving a high pressure, the period t1 is set short while the period t3 is set long so as to delay a start point and an end point of the intake action of the second plunger 3 during the compression by the first plunger 2. The drive profiles indicated with dotted lines show the case of low-pressure ejection. Since a relatively short stroke is required for achieving a low pressure, the period t1 is set long while the period t3 is set short so as to advance the start point and the end point of the intake action of the second plunger 3 during the compression by the first plunger 2.

Figure 6:
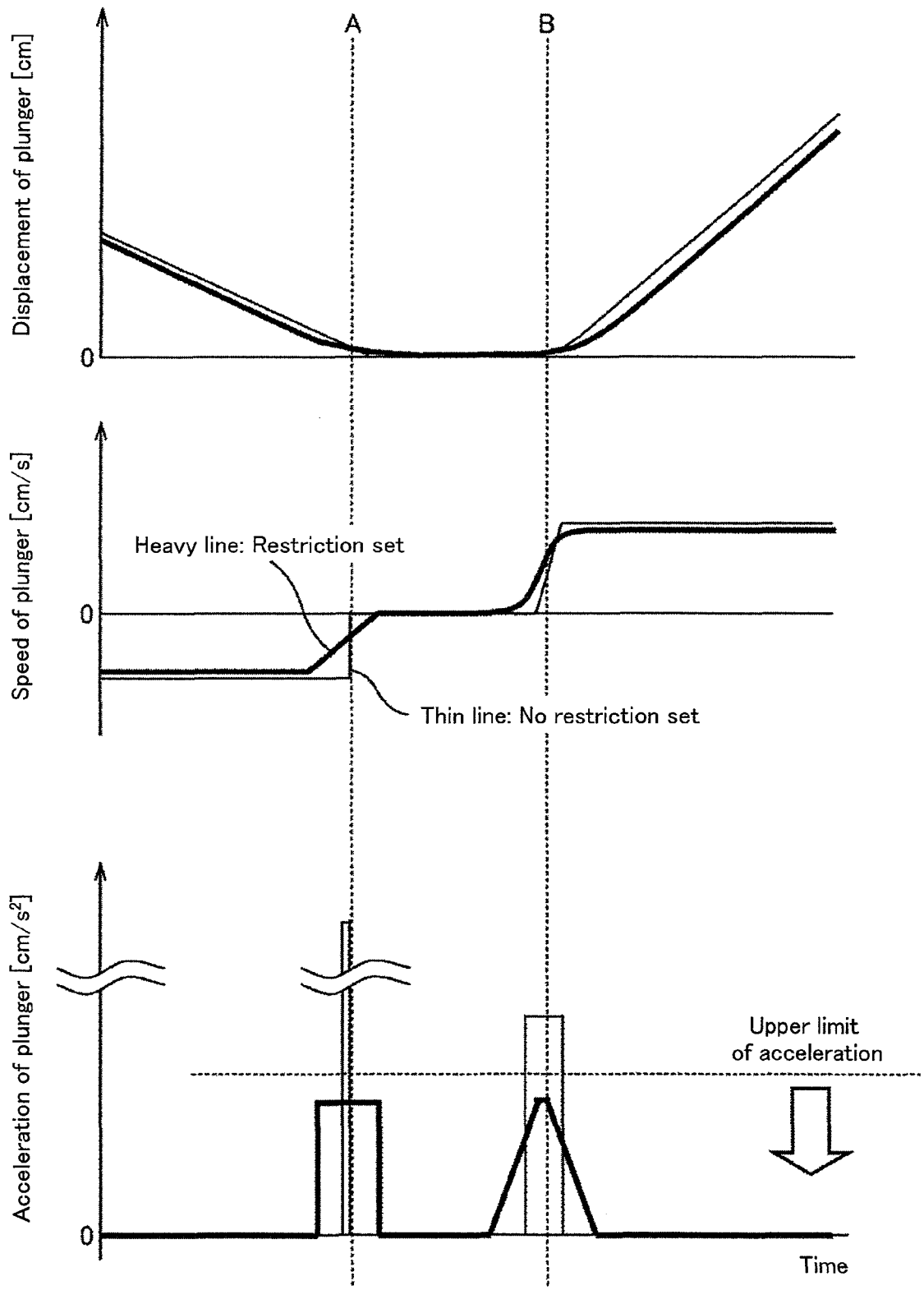
FIG. 6 shows graphs of temporal variations of displacements, speeds, and accelerations of a plunger.

FIG. 6 shows graphs of temporal variations of displacements, speeds, and accelerations of a plunger, which explain drive control of the plunger by the pump controller 50. Thin lines show the case of setting no restriction on the magnitude of an absolute value of acceleration while heavy lines show the case of setting a restriction on the magnitude of the absolute value of acceleration. In the case of setting no restriction on the acceleration indicated with the thin lines, a profile of the speed instantaneously changes from a negative value to zero at the point A. When the time required for the change in speed is zero as described above, the acceleration is theoretically infinite but an actual value becomes an extremely large value as a capacity of an actuator permits. Adoption of such an operating method is not desirable because the method may cause strong vibration attributed to the actuator or may cause water hammers or pulsations through the plungers, piping, and the like. Hence, a drive profile is set by providing the acceleration with a finite upper limit as indicated with the heavy line. Then, the speed of the plunger requires some time for the change as indicated with the heavy line. As a result, the displacement of the plunger draws a smooth locus. Next, at the point B in FIG. 6, finite acceleration values are provided both in the case of the thin line and the case of the heavy line. Here, the thin line shows an intermittent acceleration profile whereas the heavy line shows a continuous change in acceleration. If the drive profile shown at the point B with the heavy line is used when the two plunger pumps switch the intake and ejection actions, the drive profile has an advantage of suppressing a water hammer at the time of switching the ejection action. Incidentally, the respective profiles of the plunger shown in FIG. 6 are applicable to the drive profiles before and after the period t1 of the first plunger shown in any of FIG. 2, FIG. 3, and FIG. 5.

Figure 7:
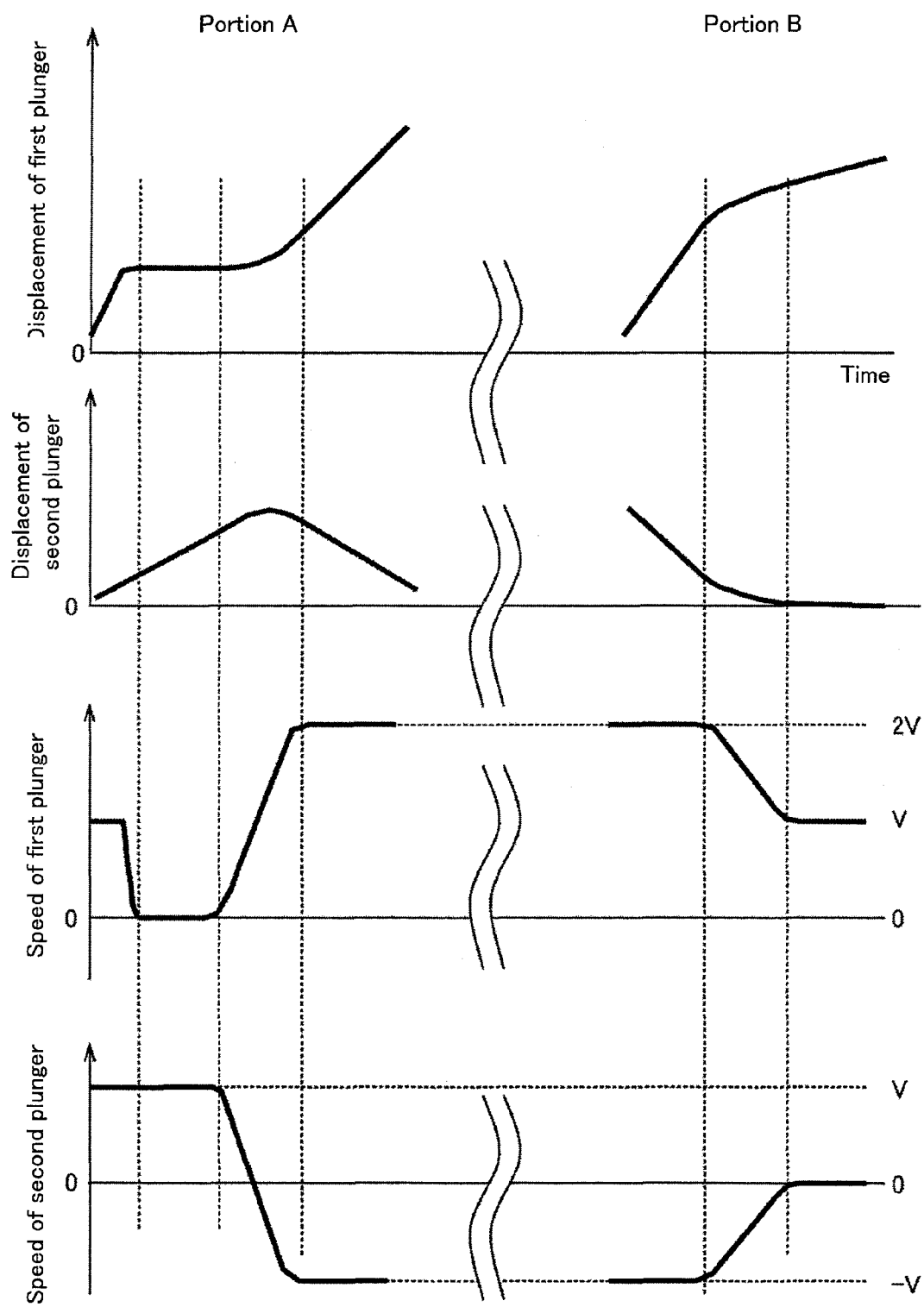
FIG. 7 shows graphs of temporal variations of displacements and speeds of the first plunger and a second plunger.
Figure 8:
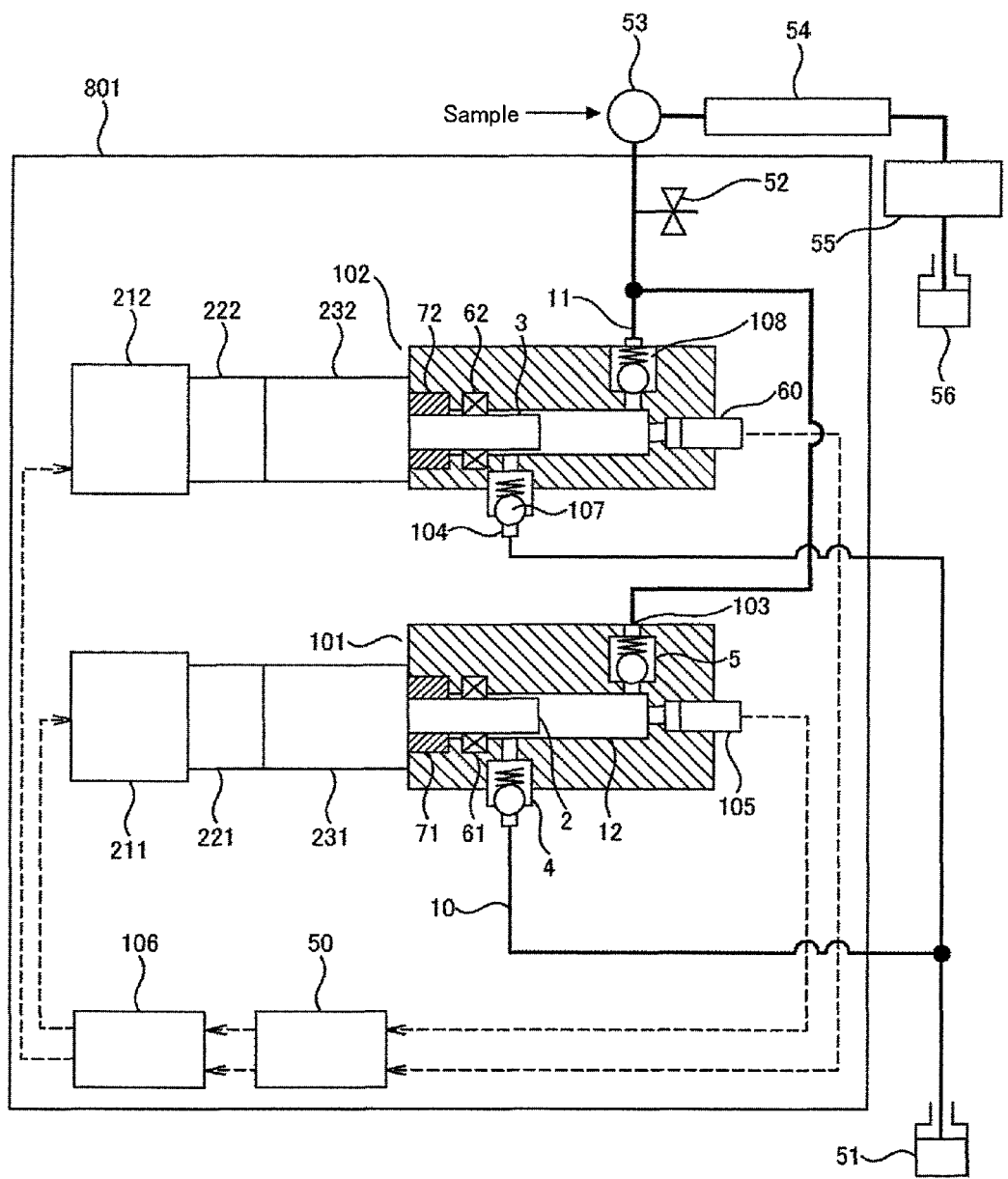
FIG. 8 is a configuration diagram showing a configuration of a liquid chromatograph.

FIG. 7 shows graphs of temporal variations of displacements and speeds of the first plunger and the second plunger. The graphs illustrate details of profiles at a portion A and a portion B indicated in FIG. 5. The graphs show, from top down, the displacement of the first plunger 2, the displacement of the second plunger 3, the speed of the first plunger 2, and the speed of the second plunger 3. The speeds smoothly change as the acceleration values are provided with upper limits in agreement with the above-described concept. What is characteristic here is that the speeds of the first plunger 2 and the second plunger 3 change in such a manner as to mutually cancel out the variations in speed. This arrangement makes it possible to switch the actions of the plungers in a transitional state of changing the speeds while maintaining the constant flow rates of ejection from the plunger pumps and providing the acceleration values with the upper limits FIG. 8 is a configuration diagram showing a configuration of a liquid chromatograph. A pump 801 for liquid chromatograph applies a configuration in which the first plunger pump 101 and the second plunger pump 102 are connected in parallel. An intake channel directed from the solvent container 51 to the pumps is divided into the first intake channel 10 and the second intake channel 104, which are connected to the first plunger pump 101 and the second plunger pump 102, respectively. In addition, the first ejection channel 103 and the second ejection channel 11 are connected to each other on the downstream side of the second plunger pump 102. Liquids pressurized by the first plunger pump 101 and the second plunger pump 102 merge at a junction between the first ejection channel 103 and the second ejection channel 11 and proceed to the separation column 54. In the first plunger pump 101, the check valve 4 is provided in the first intake channel 10 and the check valve 5 is provided in the first ejection channel 103. In the second plunger pump 102, a check valve 107 is provided in the second intake channel 104 and a check valve 108 is provided in the second ejection channel 11. An action of the first plunger pump 101 and an action of the second plunger pump 102 are controlled individually and independently of each other by the pump controller 50 and the motor driver 106. Thus, each of the plunger pumps can pressurizes the liquid independently.

Although the embodiment shown in FIG. 1 depicts an example of providing the pressure sensor 60 on the second ejection channel 11, the pressure sensor may be provided in the pressuring chamber instead as shown in FIG. 8. Specifically, the pressure sensor 105 is provided in the first pressurizing chamber 12 of the first plunger pump 101 and the pressure sensor 60 is provided in the second pressurizing chamber 13 of the second plunger pump 102. A benefit of providing the pressure sensor in the ejection channel as shown in FIG. 1 is that a volume required for installing the pressure sensor in the pressuring chamber can be eliminated to minimize a dead volume. On the other hand, a benefit of providing the pressure sensor in the pressurizing chamber as shown in FIG. 8 is a cost advantage as the structure to insert the pressure sensor directly into the pressurizing chamber can curtail a dedicated mount for installing the pressure sensor in the ejection channel. In the meantime, a difference in pressure between the pressuring chamber and the ejection channel is only about a pressure loss of a check valve as a matter of fact and an adverse effect of such a difference is negligible. Hence, a position to provide the pressure sensor may be selected without regard to accuracy of measured pressure.

Figure 9:
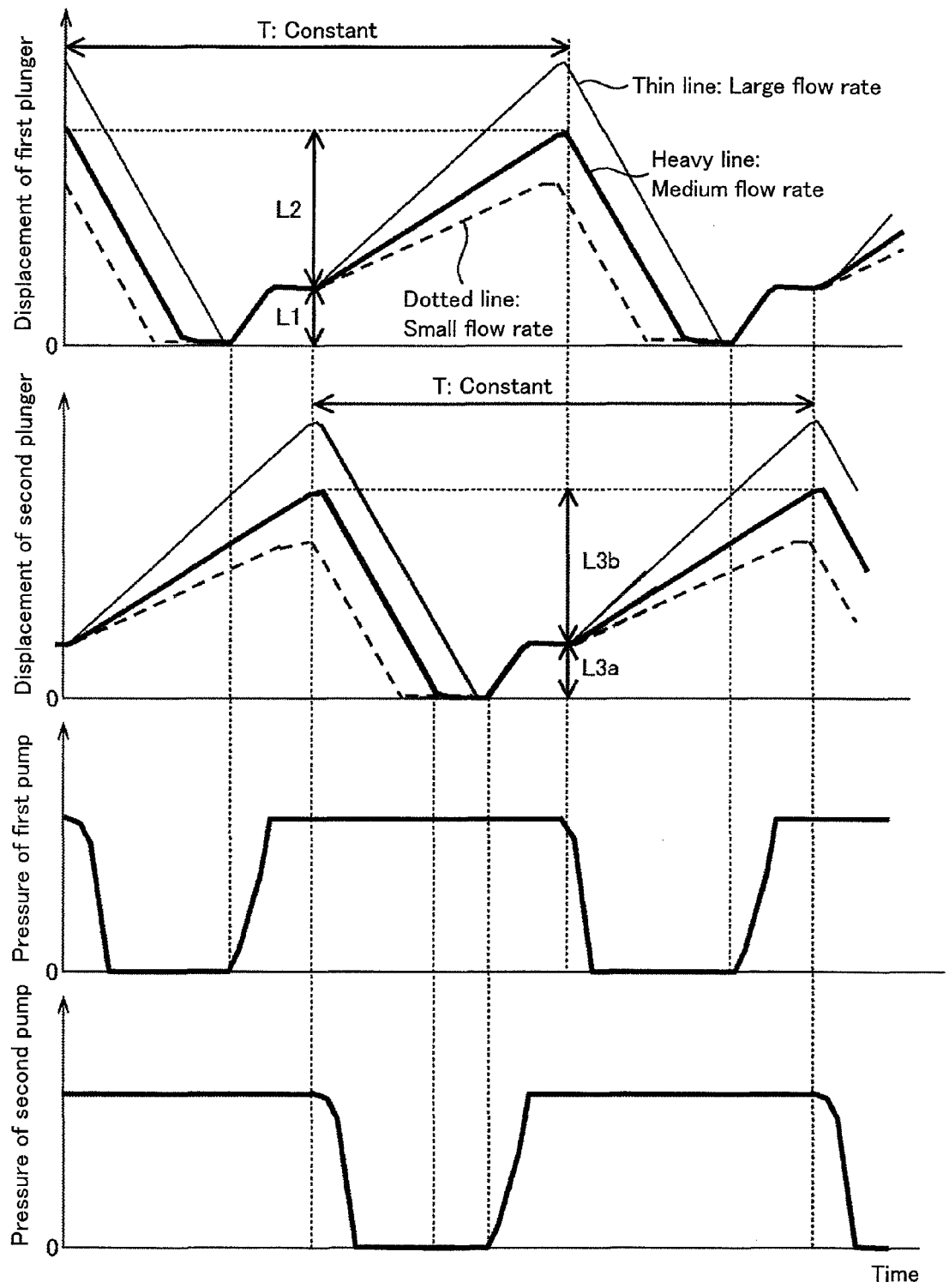
FIG. 9 shows graphs of temporal variations of displacements of plungers and a pressure of a first plunger pump.

FIG. 9 shows graphs of temporal variations of displacements of plungers and a pressure of the first pump 101 in the case where two plunger pumps are connected in parallel as shown in FIG. 8. The graphs show, from top down, displacements of the first plunger 2, displacements of the second plunger 3, a pressure in the first pressurizing chamber 12, and a pressure in the second pressurizing chamber 13. The temporal variations of the displacements and the pressures are illustrated in terms of drive profiles in three patterns, namely, of a large flow rate, a medium flow rate, and a small flow rate by using thin lines, heavy lines, and dotted lines, respectively. As basic actions, the pump controller 50 performs control in such a way that the second plunger 3 performs the compression action while the first plunger 2 is performing the intake action, and the first plunger 2 performs the compression action while the second plunger 3 is performing the intake action.

The first plunger 2 cannot perform ejection immediately after being switched from the intake action to the compression action until the pressure in the first pressurizing chamber 12 reaches the ejection pressure, i.e., the pressure in the second pressuring chamber 13. Accordingly, the second plunger 3 continues the pressure feeding action. It is preferable to once set the action speed of the first plunger 2 to zero when the pressure in the first pressurizing chamber 12 becomes equal to the pressure in the second pressurizing chamber 13. When the second plunger pump 102 terminates pressure feeding and the first plunger pump 101 starts pressure feeding, the speed of the first plunger 2 is gradually accelerated while the speed of the second plunger 3 is proportionately decelerated. This makes it possible to switch the ejecting pumps smoothly. The pump controller 50 can perform the flow rate control of the respective plunger pumps by changing a lift amount (L1+L2) of the first plunger 2 and a lift amount (L3a+L3b) of the second plunger 3. Here, if pressurizing portions of the first plunger 2 and the second plunger 3 have the same diameter and the volumes and the like of the pressurizing chambers are equal, then the lift amounts of both plungers are equal (L≈L3a, L2≈L2). If the diameter of one of the plungers is smaller, the lift amount becomes greater substantially in inverse proportion to the diameter. Meanwhile, the ejection pressure of each plunger pump can be changed by changing the lift amount for pre-compression (L1 or L3a).

Figure 10:
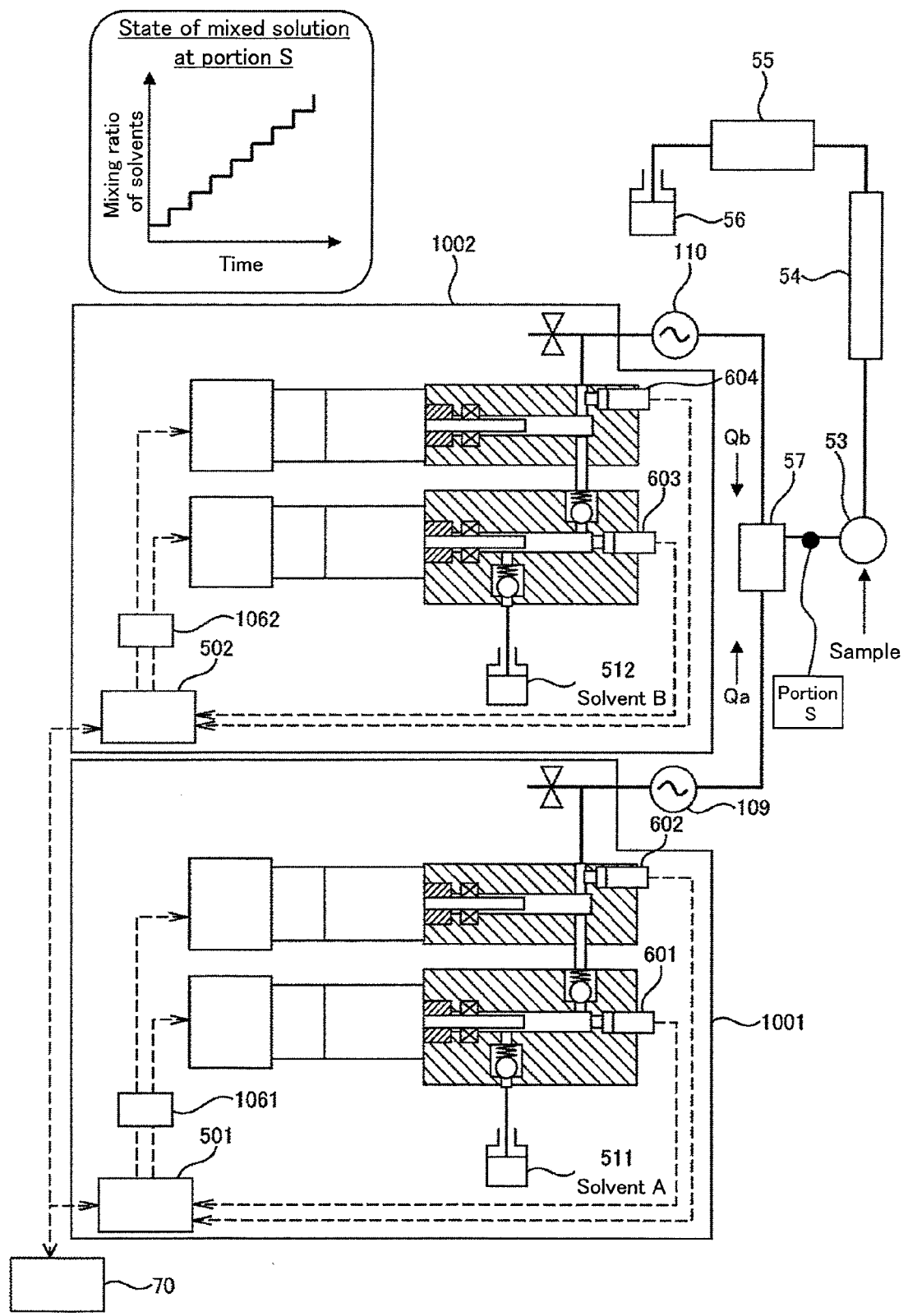
FIG. 10 is a configuration diagram showing a configuration of a liquid chromatograph constructed as a high-pressure gradient system by employing two pumps for liquid chromatograph.

FIG. 10 is a configuration diagram showing a configuration of a liquid chromatograph constructed as a high-pressure gradient system by employing two pumps for liquid chromatograph. A gradient operation means an operating method in which a mixing ratio of two types of solvents A and B is changed stepwise with time. Here, a ratio between a flow rate Qa of the solvent A in a solvent container 511 and a flow rate Qb of the solvent B in a solvent container 512 is changed while maintaining a constant total liquid feeding flow rate which is a sum of the flow rate Qa and the flow rate Qb.

In FIG. 10, a first pump 1001 for liquid chromatograph and a second pump 1002 for liquid chromatograph are connected in parallel. A pulsation absorbing damper 109 is provided in an ejection channel of the first pump 1001 for liquid chromatograph while a pulsation absorbing damper 110 is provided in an ejection channel of the second pump 1002 for liquid chromatograph. The respective solvents are mixed together by a mixer 57 and fed to an injector 53 to be mixed with a sample. The solvent mixed with the sample enters the separation column 54 to be separated into components. Then, the detector 55 detects data for a component analysis. The separation column 54 is filled with minute silica gel particles and a load pressure in a range from several tens of megapascals to more than a hundred megapascals is generated in each plunger pump due to fluid resistance of the solvent flowing through gaps among the silica gel particles. The magnitude of the load pressure varies depending on the diameter of the separation column and a flow rate of the solvent flowing therethrough.

The first pump 1001 for liquid chromatograph puts values detected by pressure sensors 601 and 602 into a pump controller 501, controls electric motors via a motor driver 1061, and thereby drives the plungers. The second pump 1002 for liquid chromatograph puts values detected by pressure sensors 603 and 604 into a pump controller 502, controls electric motors via a motor driver 1062, and thereby drives the plungers. The pump controllers 501 and 502 communicate with a host controller 70 and control the respective pumps for liquid chromatograph on the basis of instruction values from the host controller 70.

Figure 11:
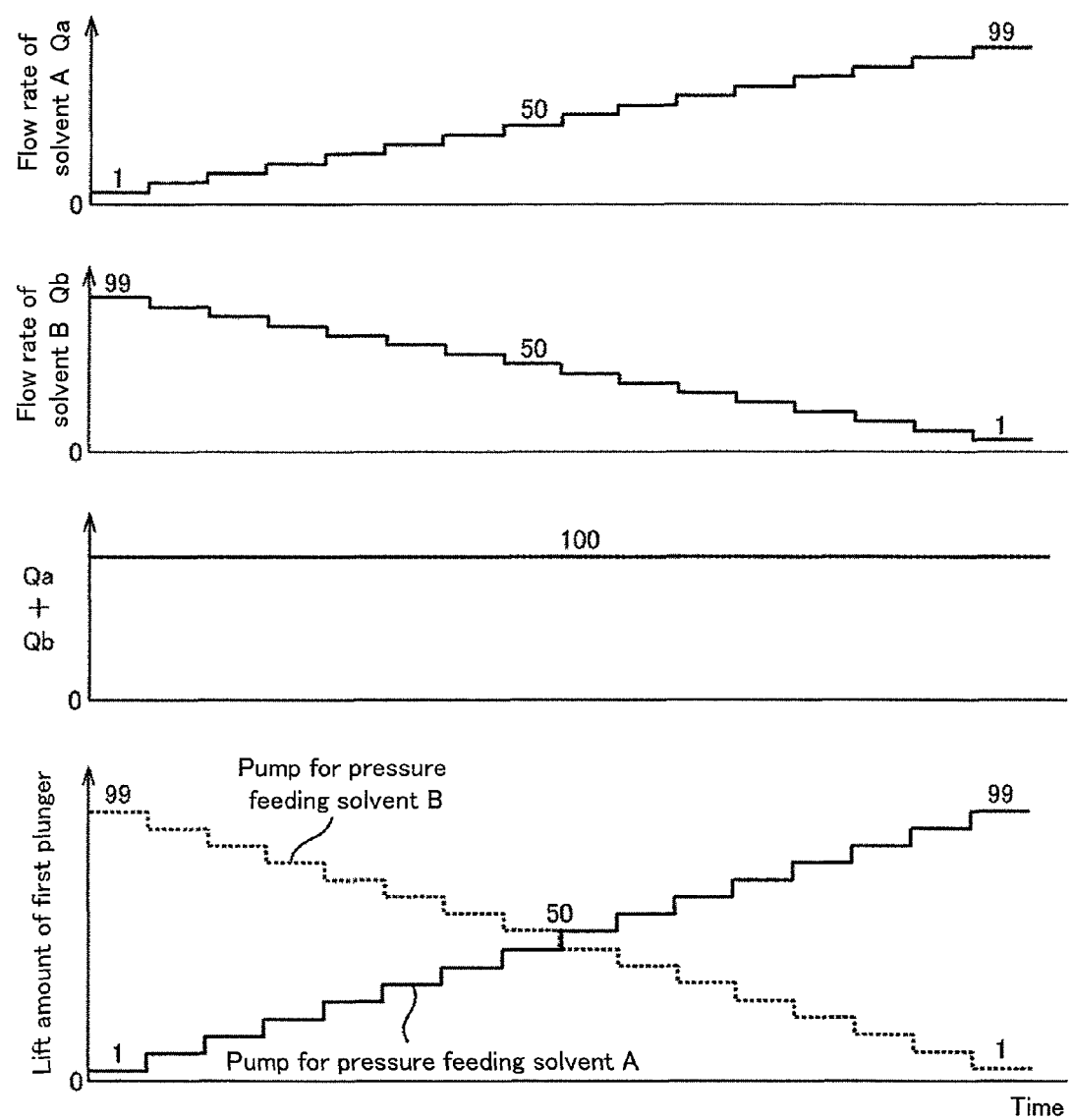
FIG. 11 shows graphs of temporal variations of flow rates of two solvents and lift amounts of first plungers in the two pumps for liquid chromatograph.

FIG. 11 shows graphs showing an example of temporal variations of flow rates of two solvents and lift amounts of the first plungers in the two pumps for liquid chromatograph. Assuming that a total flow rate is 100, for example, the temporal variation of the flow rates in a gradient operation starts with Qa:Qb=1:99, and then the mixing ratio is changed to 2:98, 3:97, . . . , 50:50, . . . , 98:2, and 99:1 as shown in FIG. 11. This is the case of 100 gradient steps. When the total liquid feeding flow rate is set to 1 mL/min, a minimum flow rate and resolution require 10 µL/min which is one-hundredth of the total liquid feeding flow rate. In order to gradually increase and decrease the flow rates of the respective pumps during the operation, the lift amounts of the plungers need to be increased and decreased in accordance with the instruction of the host controller 70 as shown at the bottom of FIG. 11.

The above-described control conducted by the host controller 70 keeps the drive cycles of the respective plunger pumps substantially constant even when the flow rates are changed, and pulsations also occur synchronously with the drive cycles. However, when the solvent A and the solvent B are mixed by the mixer 57, fluctuation in the mixing ratio attributed to the pulsations of the respective solvents can be reduced and detection accuracy on a chromatogram can be improved accordingly. Meanwhile, if a pulsation absorbing performance of the mixer 57 or the pulsation absorbing damper (not shown) has a favorable characteristic in a specific frequency range, then the solvent A and the solvent B can be well mixed by driving the respective pumps while setting the drive cycles to the frequency range. This makes it possible to improve analysis precision as a consequence. In the meantime, depending on the combination of the solvents to be mixed, there is a case where a physical property of the mixed liquid such as viscosity or density changes non-linearly with respect to the mixing ratio. A method described in Japanese Patent Application Publication No. 2004-137974 has been known as a method for dealing with this case, for example.

Figure 12:
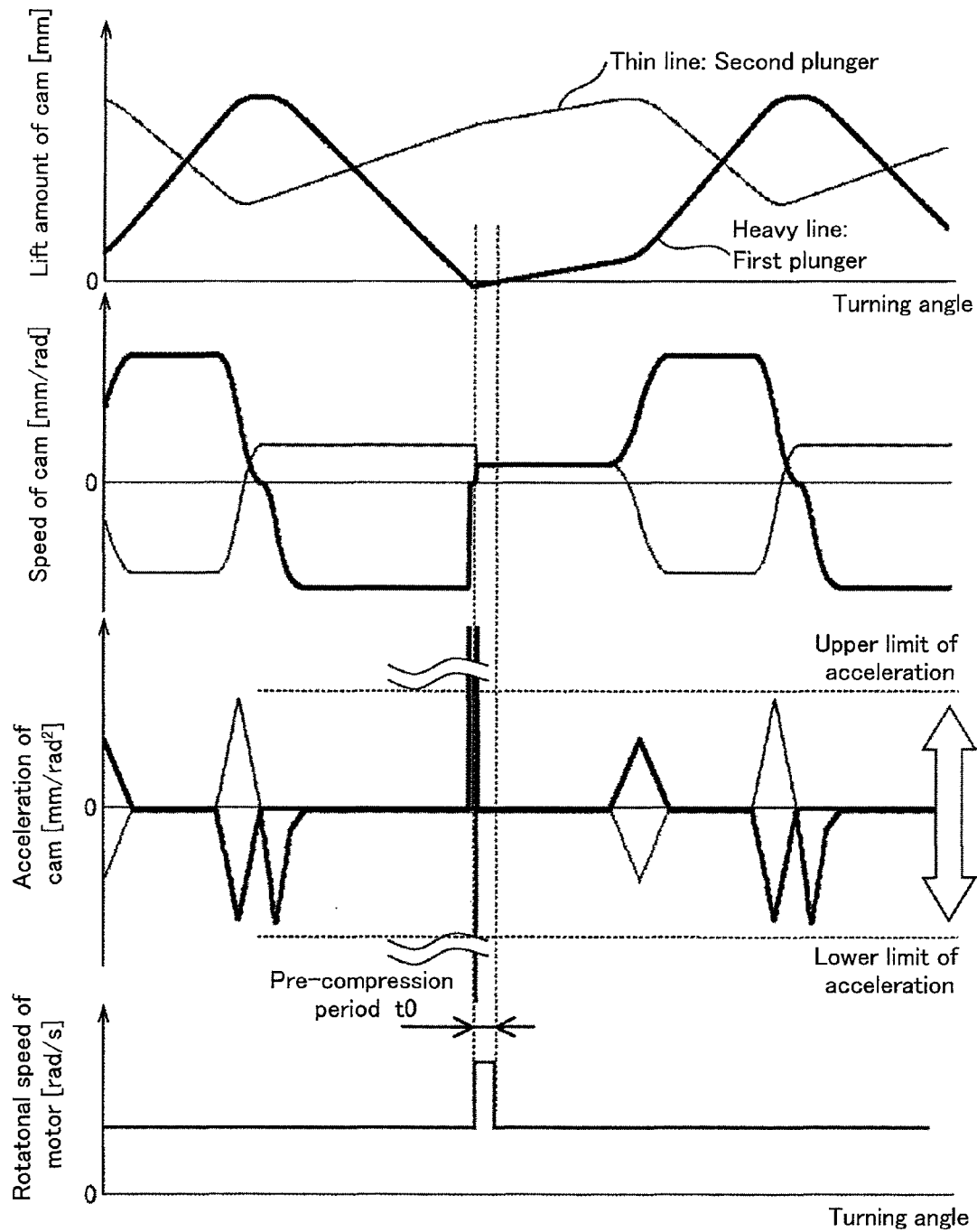
FIG. 12 shows graphs of temporal variations of lift amounts of cams for driving the plungers used in the pumps for liquid chromatograph shown in FIG. 1, rotational speeds of the cams, rotational accelerations of the cams, and a rotational speed of a drive motor.

FIG. 12 shows graphs of temporal variations of lift amounts of cams for driving the plungers used in the pumps for liquid chromatograph shown in FIG. 1, rotational speeds of the cams, rotational accelerations of the cams, and a rotational speed of a drive motor. A mechanism for converting a rotational motion of a motor into a linear motion of a plunger includes a linear motion mechanism such as a ball screw or a rack and pinion, and a cam mechanism. In the case of the linear motion mechanism, the displacement is basically proportional to a rotational angle of a rotating shaft. Since the speed or acceleration of the linear motion of the plunger is changed only by changing the rotational speed of the rotating shaft, there may be a case where desired control cannot be performed due to a difficulty in controlling the rotation of the motor. On the other hand, in the case of the cam mechanism, not only the rotation of the rotating shaft but also a cam profile can be changed, and thus a wider range of control is possible.

For instance, assuming that a lift amount of a cam is L, a rotating angle is θ, a differential value of the lift amount L of the cam is dL/dθ, and a turning angle velocity of the cam is dθ/dt, the speed of the plunger is determined by a product dL/dt of the differential value dL/dθ of the lift amount L of the cam and the turning angle velocity dθ/dt of the cam. In order to double the plunger speed, the turning angle velocity dθ/dt of the cam may be doubled or the differential value dL/dθ of the lift amount L of the cam may be doubled, for example. The settings of the respective values are selected as appropriate depending on the configuration of the pump.

The cam profiles shown in FIG. 12 represent an example to be applied to the configuration shown in FIG. 1, in which the two plungers are connected in series. The lift amount of the cams, the rotating speeds of the cams, and the rotational accelerations of the cams are regulated according to designs of the cam profiles while basically keeping the rotational speed of the motor constant. Moreover, upper and lower limits are defined in the cam acceleration profiles in order for smooth changes in the speed profiles. Meanwhile, in a pre-compression period t0 on the graphs representing a phase after terminating the intake action and before starting the compression action by the first plunger, the rotational speed of the motor is doubled while the cam speed for the second plunger is reduced to half. A reason for thus changing the speeds is that the requisite pre-compression period varies depending on the ejection pressure, the physical properties of the liquid, and so forth. Accordingly, this period is dealt with by controlling the rotation of the motor according to need. If the pre-compression period t0 is long or in the case of compression up to a high pressure, for example, the rotational speed of the motor may be doubled until termination of the pre-compression. This makes it possible to drive the second plunger at a constant speed and to pressure feed a liquid at a constant flow rate even though the cam speed for the second plunger is reduced to half. Here, duration of pre-compression for the first plunger can also be reduced by doubling the speed of the pre-compression for the first plunger during this period. In other words, the first plunger and the second plunger do not have to be controlled independently. Thus, it is possible to construct the pump by providing only one motor.

As described above, the embodiment according to the present invention provides a pump for liquid chromatograph including two plunger pumps connected in series or in parallel and configured to perform intake and compression actions alternately and to perform liquid feeding continuously at a constant flow rate. Here, the pump adopts a configuration in which a pressuring chamber of one of the plunger pumps is always set to a state of high pressure and a pump controller performs flow rate control by adjusting lift amounts of a first plunger and a second plunger. This configuration is capable of reducing pulsations even when an ejection flow rate is changed, and of avoiding transmission of the pulsations to a separation column. Thus, it is possible to prevent degradation in analysis precision of a liquid chromatograph.

EXPLANATION OF REFERENCE NUMERALS 1, 801 PUMP FOR LIQUID CHROMATOGRAPH
2 FIRST PLUNGER

3 SECOND PLUNGER
4, 5, 107, 108 CHECK VALVE
10 FIRST INTAKE CHANNEL
11 SECOND INJECTION CHANNEL
12 FIRST PRESSURIZING CHAMBER
13 SECOND PRESSURIZING CHAMBER
50, 501, 502 PUMP CONTROLLER
51, 511, 512, SOLVENT CONTAINER
52 DISCHARGE VALVE
53 INJECTOR
54 SEPARATION COLUMN
55 DETECTOR
56 WASTE CONTAINER
67 MIXER
60, 105, 601, 602, 603, 604 PRESSURE SENSOR
61, 62 SEALING
70 HOST CONTROLLER
71, 72 BEARING
101 FIRST PLUNGER PUMP
102 SECOND PLUNGER PUMP
103 FIRST EJECTION CHANNEL
104 SECOND INTAKE CHANNEL
106 MOTOR DRIVER
109, 110 PULSATION ABSORBING DAMPER
212, 212 ELECTRIC MOTOR
221, 222 DECELERATION DEVICE
231, 232 LINEAR MOTION DEVICE
1001 FIRST PUMP FOR LIQUID CHROMATOGRAPH
1002 SECOND PUMP FOR LIQUID CHROMATOGRAPH

All the publications, patents, and patent applications cited in this specification are incorporated in this specification by reference.

The invention claimed is:

1. A pump for liquid chromatograph characterized in that the pump comprises:
   a first plunger pump including, a first pressurizing chamber communicating with a first intake channel and a first ejection channel, and a first plunger configured to reciprocate inside the first pressurizing chamber;
   a second plunger pump including, a second pressurizing chamber communicating with a second intake channel and a second ejection channel, and a second plunger configured to reciprocate inside the second pressurizing chamber;
   a connection flow channel connecting the first plunger pump and the second plunger pump in series or in parallel;
   at least one electric motor configured to generate rotative power;
   a power transmission mechanism configured to convert the rotative power of the electric motor into linear reciprocating power and to transmit the power to the first plunger and the second plunger;
   the power transmission mechanism is formed of a cam;
   wherein the power transmission mechanism is configured to adopt a cam phase in which a differential value $dL/d\theta$ of a rotational angle $\theta$ relative to a lift amount L of the cam varies, the cam phase being established by changing a rotational speed of the electric motor in such a manner that a product of the differential value $dL/d\theta$ and the rotational speed of the electric motor becomes substantially constant as compared to values preceding and subsequent thereto;
   a motor driver configured to control the electric motor;
   at least one pressure detecting means provided in the first pressurizing chamber, the second pressure chamber, or a channel on a downstream side of any of the pressuring chambers; and
   a pump controller configured to read a measurement value of the pressure detecting means, to provide the motor driver with an instruction value, to cause the first plunger pump and the second plunger pump to perform intake and compression actions alternately at substantially constant time cycles, to set the pressurizing chamber of one of the plunger pumps to a state of a higher pressure during compression than the pressurizing chamber of the other plunger pump during compression, and to perform flow rate control by adjusting stroke lengths of the first plunger and the second plunger.

2. The pump for liquid chromatograph according to claim 1, characterized in that
   a resting period is provided in which an action speed of the second plunger is set to zero, and
   high-pressure liquid feeding is performed only with the first plunger pump during the resting period.

3. The pump for liquid chromatograph according to claim 2, characterized in that the pump controller performs control in such a manner as to adjust a length of the resting period and the lift amount of the first plunger depending on at least an amount of liquid feeding, a pressure, a type of a medium, and an operating state of the pump.

4. The pump for liquid chromatograph according to claim 1, characterized in that the pump controller performs control in such a manner that the first plunger maintains a state in which an action speed is set to zero for a predetermined period within a time between a timing when the first plunger pump terminates an intake action and a timing when the second plunger pump terminates a compression action.

5. The pump for liquid chromatograph according to claim 4, characterized in that the pump controller changes the period in which the action speed is set to zero and keeps drive time cycles of the first plunger pump and the second plunger pump substantially constant.

6. The pump for liquid chromatograph according to claim 1, characterized in that the pump controller performs control in such a manner that a speed of the first plunger is set to zero at a point of time when a pressure of the first plunger pump is substantially equal to a pressure of the second plunger pump.

7. The pump for liquid chromatograph according to claim 1, characterized in that the pump controller performs control by setting a specific upper limit value to an absolute value of acceleration of each of the first plunger and the second plunger.

8. The pump for liquid chromatograph according to claim 1, characterized in that the pump controller sets speeds of the first plunger and the second plunger to zero at a point of time when a pressure of the first plunger pump is substantially equal to a pressure of the second plunger pump.

9. The pump for liquid chromatograph according to claim 1, characterized in that
   the first ejection channel is connected to the second intake channel, and
   each of the first intake channel and the first ejection channel is provided with a check valve.

10. The pump for liquid chromatograph according to claim 1, characterized in that
    the first ejection channel is connected to the second ejection channel,
    the first intake channel is connected to the second intake channel, and each of the first intake channel, the second intake channel, the first ejection channel, and the second ejection channel is provided with a check valve.

11. The pump for liquid chromatograph according to claim 1, characterized in that
when an amount of liquid feeding by the first plunger pump changes and an amount of liquid feeding by the second plunger pump changes, the pump controller controls the amounts of liquid feeding by adjusting the lift amounts of the first plunger and the second plunger in such a manner as to keep drive time cycles of the first plunger and the second plunger substantially constant.

12. The pump for liquid chromatograph according to claim 1, characterized in that
the pump comprises the two electric motors which drive the first plunger pump and the second plunger pump independently of each other.

13. The pump for liquid chromatograph according to claim 1, wherein the pump controller is further configured to provide a first resting period in which an action speed of the first plunger is set to zero and a second resting period in which an action speed of the second plunger is set to zero, and wherein first resting period is a predetermined period between when the first plunger pump terminates an intake action and when the second plunger pump terminates a compression action.

14. A pump for liquid chromatograph characterized in that the pump comprises:
a first plunger pump and a second plunger pump connected in series or in parallel;
at least one electric motor configured to generate rotative power;
a power transmission mechanism configured to convert the rotative power of the electric motor into linear reciprocating power and to transmit the power to the first plunger and the second plunger;
the power transmission mechanism is formed of a cam;
wherein the power transmission mechanism is configured to adopt a cam phase in which a differential value $dL/d\theta$ of a rotational angle $\theta$ relative to a lift amount L of the cam varies, the cam phase being established by changing a rotational speed of the electric motor in such a manner that a product of the differential value $dL/d\theta$ and the rotational speed of the electric motor becomes substantially constant as compared to values preceding and subsequent thereto;
a pump controller, and
the pump controller causes the first plunger pump and the second plunger pump, connected in series or in parallel, to perform intake and compression actions alternately at substantially constant time cycles, sets a pressurizing chamber of one of the plunger pumps to a state of a higher pressure during compression than a pressurizing chamber of the other plunger pump during compression, and performs flow rate control by adjusting stroke lengths of the first plunger and the second plunger.

15. The pump for liquid chromatograph according to claim 14, wherein the pump controller is further configured to provide a first resting period in which an action speed of the first plunger is set to zero and a second resting period in which an action speed of the second plunger is set to zero, and wherein first resting period is a predetermined period between when the first plunger pump terminates an intake action and when the second plunger pump terminates a compression action.

16. A liquid chromatograph including:
a first pump configured to feed a first eluent;
a second pump configured to feed a second eluent;
a mixer configured to mix the first eluent and the second eluent;
an injector configured to inject a sample into the eluents mixed by the mixer;
a separation column configured to separate the sample injected into the eluents into components; and
a detector configured to allow inflow of the eluents, in which the sample is separated into the components, and to detect the components by irradiating the eluents with light,
the liquid chromatograph characterized in that
each of the first pump and the second pump includes:
a first plunger pump and a second plunger pump connected in series or in parallel;
a pump controller;
at least one electric motor configured to generate rotative power;
a power transmission mechanism configured to convert the rotative power of the electric motor into linear reciprocating power and to transmit the power to the first plunger and the second plunger;
the power transmission mechanism is formed of a cam;
wherein the power transmission mechanism is configured to adopt a cam phase in which a differential value $dL/d\theta$ of a rotational angle $\theta$ relative to a lift amount L of the cam varies, the cam phase being established by changing a rotational speed of the electric motor in such a manner that a product of the differential value $dL/d\theta$ and the rotational speed of the electric motor becomes substantially constant as compared to values preceding and subsequent thereto; and
wherein each of the pump controllers causes the corresponding first plunger pump and the corresponding second plunger pump to perform intake and compression actions alternately at substantially constant time cycles, sets a pressurizing chamber of one of the plunger pumps to a state of a higher pressure during compression than a pressurizing chamber of the other plunger pump during compression, and performs flow rate control by adjusting stroke lengths of the corresponding first plunger and the corresponding second plunger.

17. The liquid chromatograph according to claim 16, wherein each of the pump controllers is further configured to provide a first resting period in which an action speed of the first plunger is set to zero and a second resting period in which an action speed of the second plunger is set to zero, and wherein first resting period is a predetermined period between when the first plunger pump terminates an intake action and when the second plunger pump terminates a compression action.

* * * * *